United States Patent
Edwards et al.

(10) Patent No.: US 10,653,809 B2
(45) Date of Patent: May 19, 2020

(54) SCENT DISPENSING DEVICE

(71) Applicant: VAPOR COMMUNICATIONS, INC., Cambridge, MA (US)

(72) Inventors: David A. Edwards, Cambridge, MA (US); Rachel Diane Field, Huntington Beach, CA (US); Julien Benayoun, Paris (FR); William Boujon, Paris (FR)

(73) Assignee: ONOTES, INC., Boston, MA (US)

( * ) Notice: Subject to any disclaimer, the term of this patent is extended or adjusted under 35 U.S.C. 154(b) by 126 days.

(21) Appl. No.: 15/550,720

(22) PCT Filed: Feb. 12, 2016

(86) PCT No.: PCT/US2016/017781
§ 371 (c)(1),
(2) Date: Aug. 11, 2017

(87) PCT Pub. No.: WO2016/130937
PCT Pub. Date: Aug. 18, 2016

(65) Prior Publication Data
US 2018/0036449 A1  Feb. 8, 2018

Related U.S. Application Data

(60) Provisional application No. 62/116,258, filed on Feb. 13, 2015, provisional application No. 62/153,936, filed on Apr. 28, 2015.

(51) Int. Cl.
*A61L 9/00* (2006.01)
*B01F 3/04* (2006.01)
(Continued)

(52) U.S. Cl.
CPC .............. *A61L 9/127* (2013.01); *A61L 9/012* (2013.01); *A61L 9/122* (2013.01);
(Continued)

(58) Field of Classification Search
CPC .......... B01F 3/04; B01F 3/04085; A61L 9/00
(Continued)

(56) References Cited

U.S. PATENT DOCUMENTS

| 4,014,501 A | * | 3/1977 | Buckenmayer | ........ B65D 85/00 239/58 |
| 5,805,768 A | | 9/1998 | Schwartz et al. | |

(Continued)

FOREIGN PATENT DOCUMENTS

EP  2 832 375 A1  2/2015

OTHER PUBLICATIONS

International Search Report, dated Jun. 2, 2016, for PCT/US2016/017781, 3 pages.

(Continued)

*Primary Examiner* — Robert A Hopkins
(74) *Attorney, Agent, or Firm* — Cozen O'Connor

(57) ABSTRACT

A scent dispensing device is disclosed. The scent dispensing device has a housing that has a cavity which forms an interior of the housing and separates the interior from an external environment. The cavity may be sized and dimensioned to receive at least one scent cartridge. The housing may have a number of apertures that each provide a respective flow path between the interior of the housing and the external environment. A number of selectively permeable membranes may be positioned in the flow paths. The selectively permeable membranes may selectively block moisture from reaching the interior of the housing from the external environment and may permit passage of gas between the interior of the housing and the external environment including passage of at least one scent from the interior of the housing to the external environment.

26 Claims, 13 Drawing Sheets

(51) Int. Cl.
*A61L 9/12* (2006.01)
*A61L 9/012* (2006.01)
*D06M 13/00* (2006.01)

(52) U.S. Cl.
CPC ..... *B01F 3/04085* (2013.01); *A61L 2209/133* (2013.01); *A61L 2209/14* (2013.01); *D06M 13/005* (2013.01)

(58) Field of Classification Search
USPC ........................................ 239/53, 55; 261/30
See application file for complete search history.

(56) References Cited

U.S. PATENT DOCUMENTS

| | | |
|---|---|---|
| 8,485,454 B1 | 7/2013 | Irvin et al. |
| 2010/0193542 A1 | 8/2010 | Macler |
| 2014/0230313 A1 | 8/2014 | Elman |

OTHER PUBLICATIONS

Written Opinion, dated Jun. 2, 2016, for PCT/US2016/017781, 10 pages.

\* cited by examiner

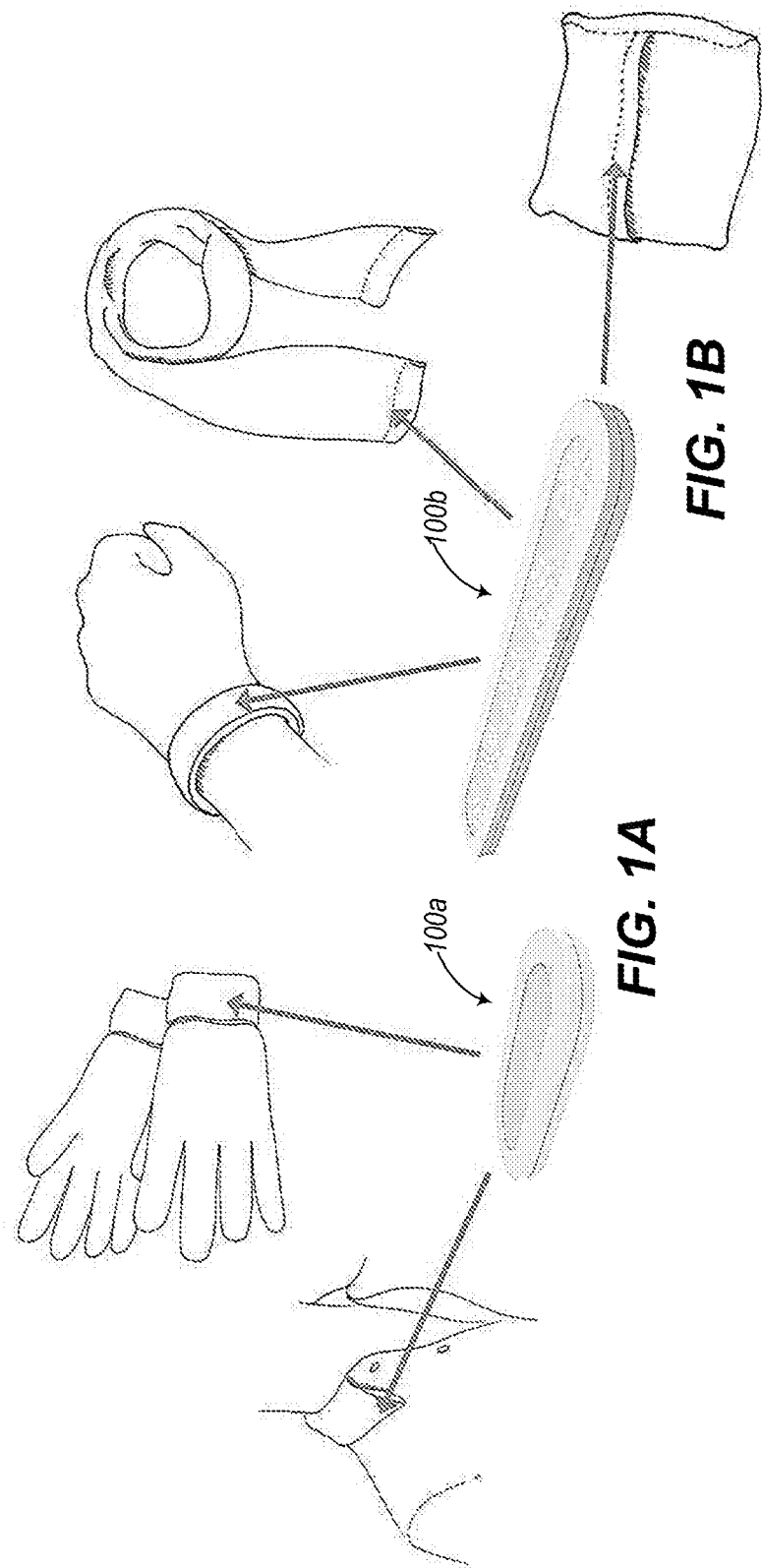

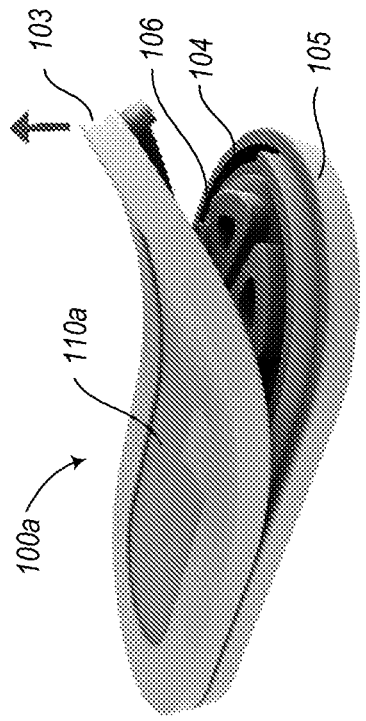
FIG. 2A
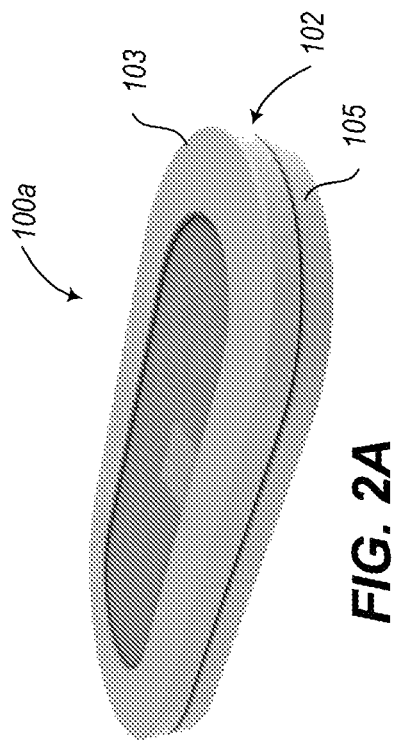
FIG. 2B
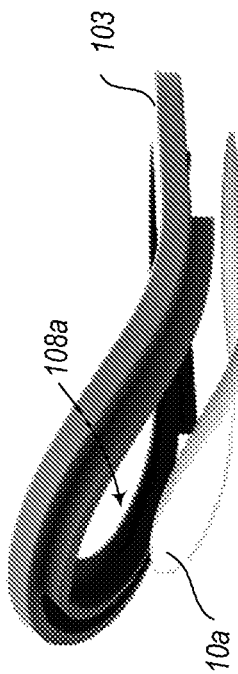
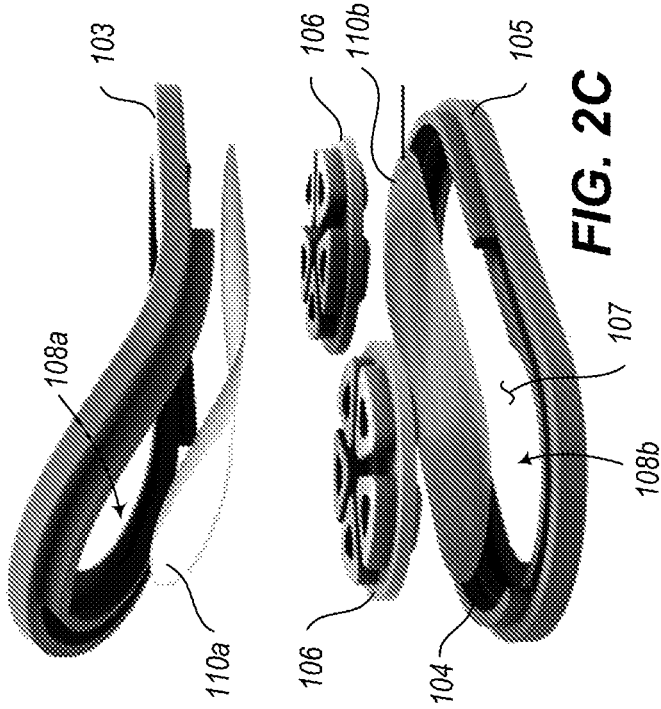
FIG. 2C

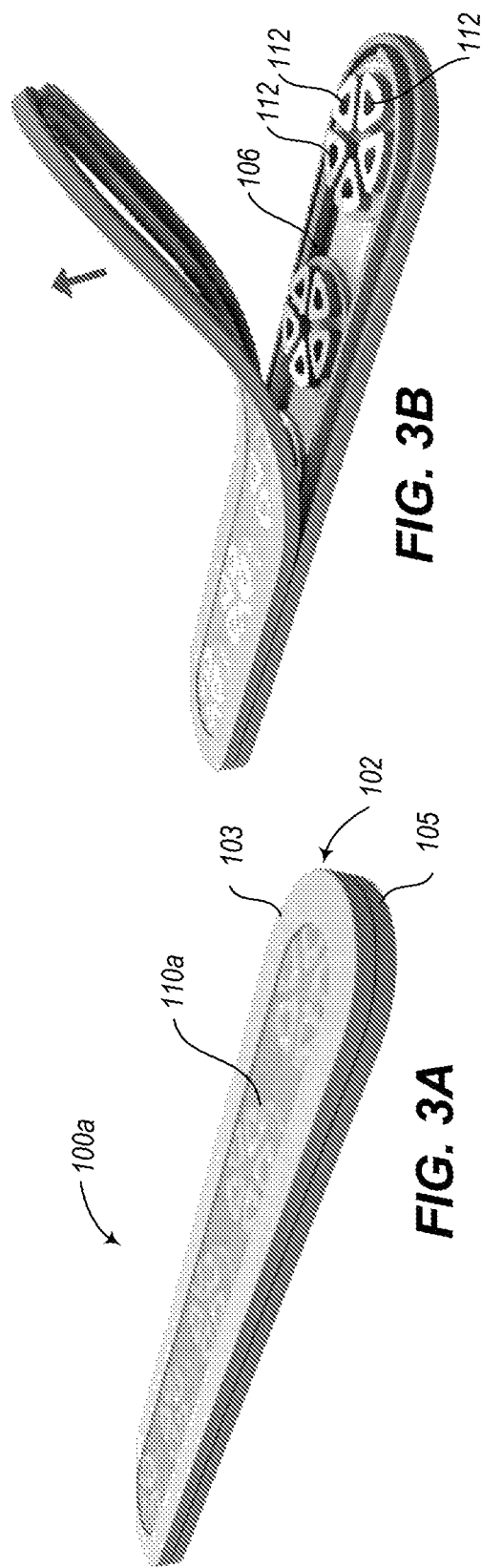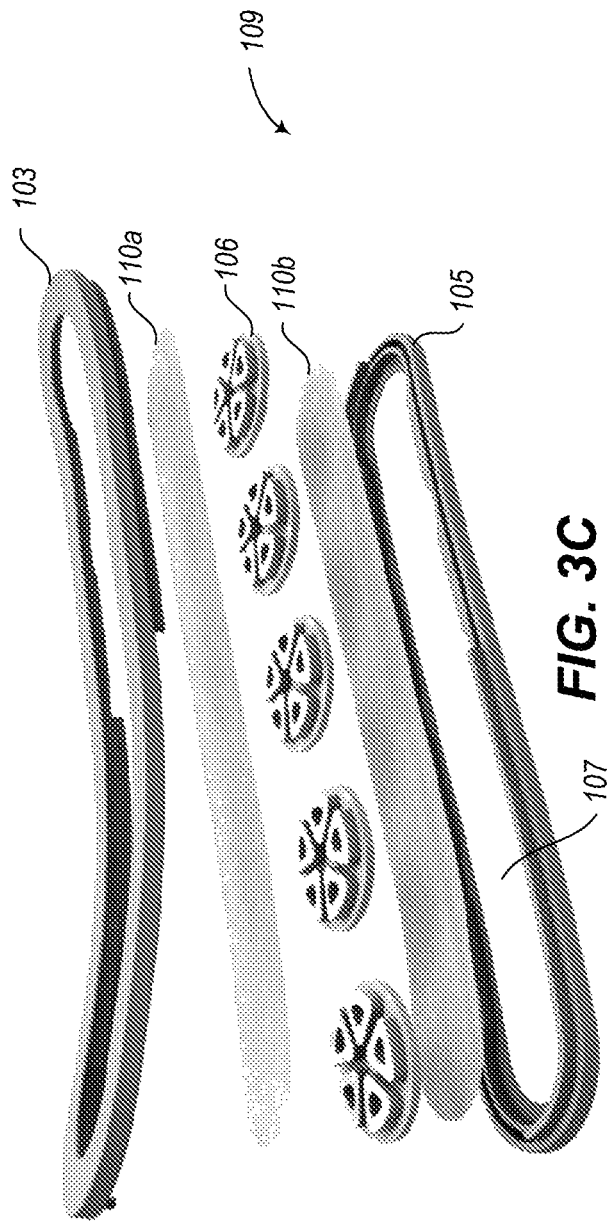

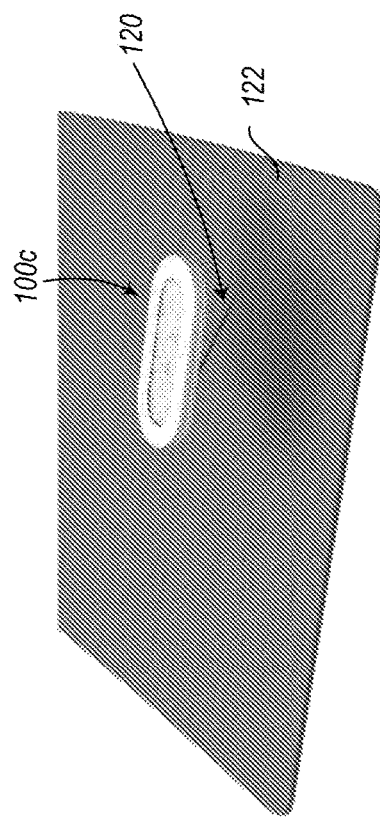
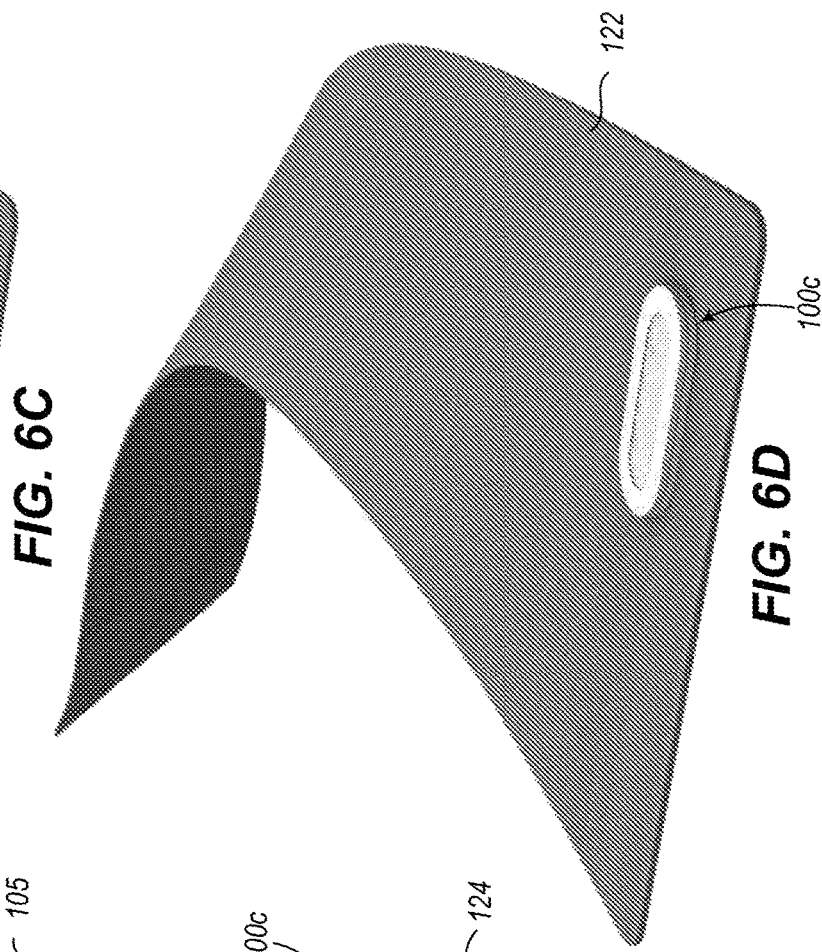
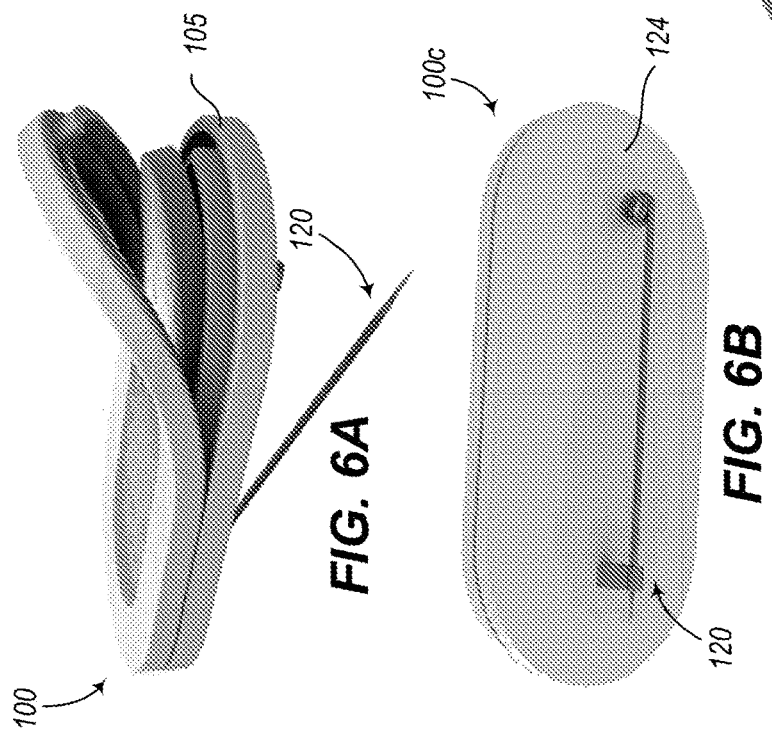

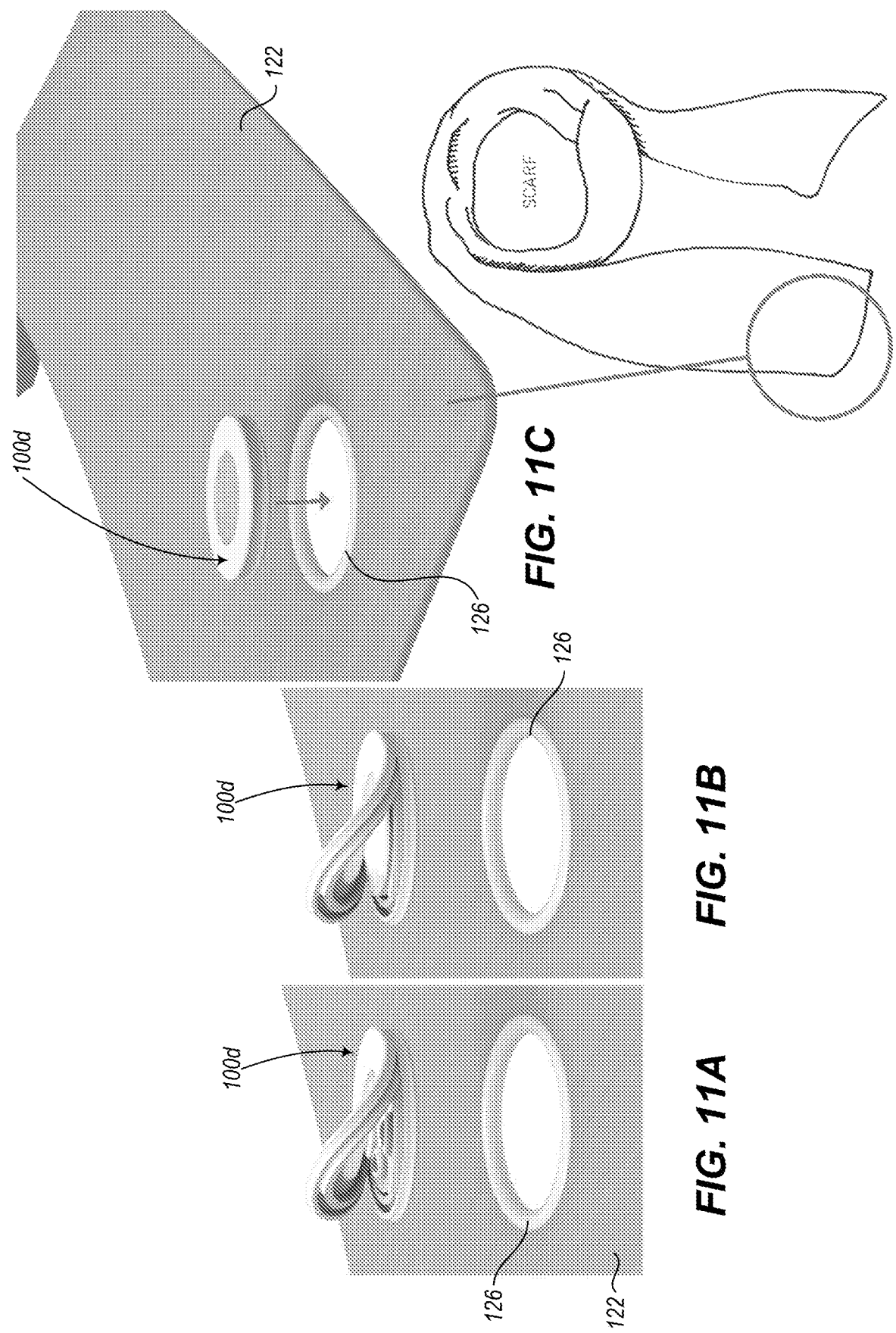

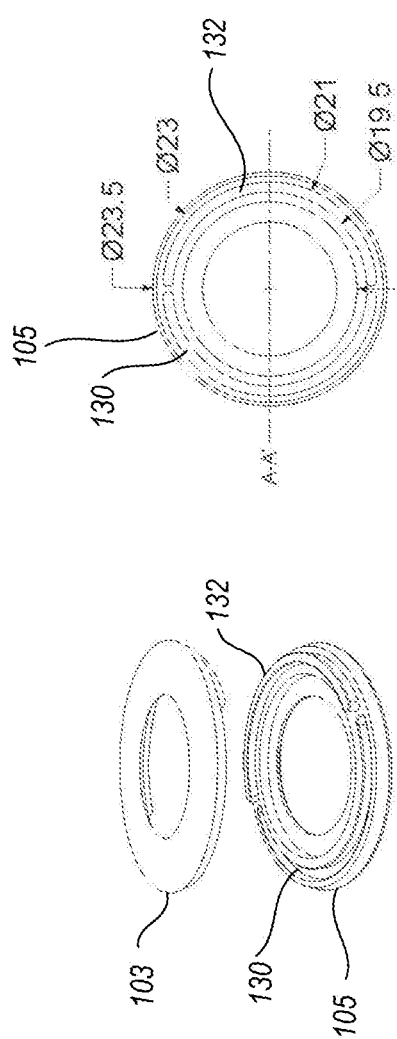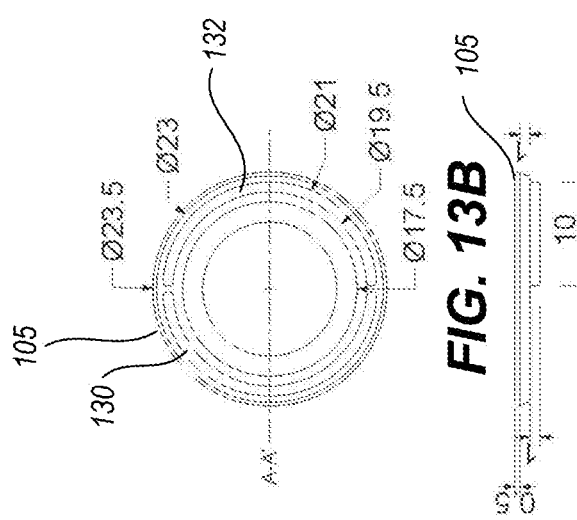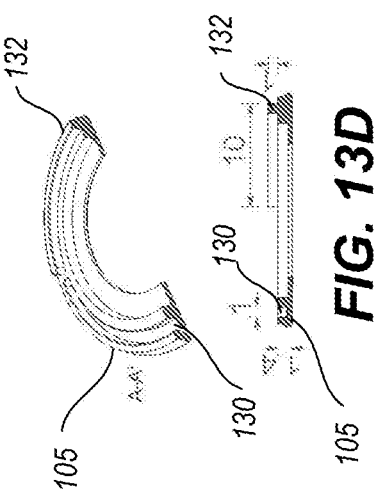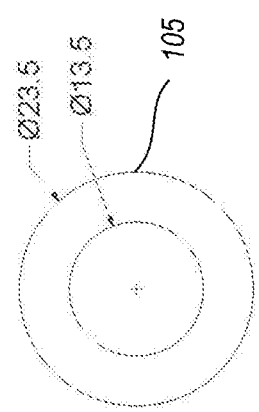

SCENT DISPENSING DEVICE

BACKGROUND

Technical Field

The present disclosure relates generally to storing and transporting scent cartridges.

Description of the Related Art

The sense of smell (i.e., olfactory perception) is extremely important to humans. For example, the smell of smoke can alert a person of the potential dangers of a nearby fire. Additionally, smells can trigger memories and impact our emotions. Various forms of aromatherapy have been investigated in attempts to alter a person's mind, mood, cognitive function, and/or health.

A number of systems and devices have been developed for selectively providing olfactory sensations. For a variety of reasons, such systems and devices have proven to be inadequate and have not gained commercial acceptance. For example, the Smell-O-Vision system was developed over fifty years ago, which caused a number of different odors to be emitted from the seats in a movie theater when triggered by a film's soundtrack. That system was expensive and had technical problems. Accordingly, the Smell-O-Vision system was used in conjunction with only one film.

New approaches that enable users to quickly and easily generate customized scent specifications for communicating specific themes, ideas, and/or feelings using sequences and combinations of scents are desirable. Additionally, new systems and devices that dispense scents based on such scent specifications are desirable.

BRIEF SUMMARY

A scent dispensing device may be summarized as including a housing that has a cavity which forms an interior of the housing and which separates the interior from an external environment which is external to the housing, the cavity sized and dimensioned to receive at least one scent cartridge therein, the housing having a number of apertures which provide respective ones of a number of flow paths between the interior of the housing and the external environment; and a number of selectively permeable membranes positioned in the flow paths, the selectively permeable membranes which selectively block moisture from reaching the interior of the housing from the external environment, and which permit passage of gas between the interior of the housing and the external environment including passage of at least one scent from the interior of the housing to the external environment. The housing may include at least one scent cartridge receiver, the at least one scent cartridge receiver sized and dimensioned to secure the at least one scent cartridge in the cavity of the housing.

The scent dispensing device may further include at least one scent cartridge which carries at least one scent media, the at least one scent cartridge securely received by the at least one scent cartridge receiver.

The scent dispensing device may further include at least one scent cartridge which carries at least one scent media, the at least one scent cartridge securely removably received by the at least one scent cartridge receiver. At least one selectively permeable membrane may be a hydrophobic membrane.

The at least one scent cartridge may carry a first scent media and at least a second scent media, the second scent media different from the first scent media. The first scent media may comprise a fibrous material (e.g., felt or other nonwoven material, clumps, woven or knitted material) saturated with a scent or fragrance (e.g., essential oil). The second scent media may comprise a wax or similar material bearing scent particles. The scent particles may be suspended in the wax material. The saturated fibrous material may be positioned in the at least one scent cartridge toward an output face of the scent cartridge relative to the wax material, in use the output face intended to be placed relatively closer to a nose in use than an opposed face of the output cartridge.

The scent dispensing device may further include at least one of a fan or a synthetic jet positioned and selectively operable to cause a flow of air between the interior of the housing and the external environment to diffuse scent into the external environment.

The scent dispensing device may further include an interface that transfers data to the scent dispensing device. The data may specify at least one of a selection of the scent provided by the scent dispensing device or a setting of at least one of a fan or a synthetic jet of the scent dispensing device, the setting indicating an operational mode of the at least one of a fan or a synthetic jet. At least one portion of at least an exterior of the housing may be resiliently deformedly physically securable in an internal contour of at least a portion of an object to which the scent dispensing device is physically securable. The at least one scent may passively diffuse along the flow path and through the selectively permeable membranes positioned in the flow path. The at least one scent may be passively convectively conveyed along the flow path and through the selectively permeable membranes positioned in the flow path.

A scent dispensing device may be summarized as including a housing that has a cavity that forms an interior of the housing, the housing which separates the interior from an external environment which is external to the housing, the interior sized and dimensioned to receive one or more scent cartridges, the housing having at least one portion that is resiliently deformedly physically securable in an internal contour of at least a portion of an object to which the scent dispensing device is physically securable. The housing may be removably physically secured to the object via at least a friction or an interference fit therewith.

The scent dispensing device may further include one or more scent cartridges disposed in the interior of the scent dispensing device, at least one of the one or more scent cartridges carries one or more scent media.

The housing may further include at least one scent cartridge receiver, the at least one scent cartridge receiver sized and dimensioned to removably secure the at least one scent cartridge in the cavity of the housing.

The housing may have a number of apertures which provide respective ones of a number of flow paths between the interior of the housing and the external environment, and may further include a number of selectively permeable membranes positioned in the flow paths, the selectively permeable membranes which selectively block moisture from reaching the interior of the housing from the external environment, and which permit passage of gas between the interior of the housing and the external environment including passage of at least one scent from the interior of the housing to the external environment.

The scent dispensing device may include at least one scent cartridge that carries a first scent media and at least a second scent media, the second scent media different from the first scent media. The first scent media may comprise a fibrous material (e.g., felt or other nonwoven material, clumps, woven or knitted material) saturated with a scent or fragrance (e.g., essential oil). The second scent media may comprise a wax or similar material bearing scent particles. The scent particles may be suspended in the wax material.

A scent dispensing device may be summarized as including a grommet having a passage; and a housing removably resiliently securable at least partially in the passage of the grommet, the housing having a cavity, the housing separates an interior of the cavity from an external environment, the interior is sized and dimensioned to hold scent media therein for release to the external environment. The grommet may be attached to a textile, and at least a portion of the housing may be resiliently deformable to removably physically secure the housing at least partially in the passage of the grommet. The housing may include an upper portion and a lower portion, the upper portion and the lower portion may be removably coupled to one another to enable removable replacement of at least one scent cartridge which carries the scent media. At least one of the upper portion or the lower portion may have a first surface with groove disposed thereon, the groove may be sized and dimensioned to receive a tongue disposed on a second surface of at least another one of the upper portion or the lower portion and removably hold the at least another one of the upper portion or the lower portion. The housing may have one or more apertures, an aperture of the one or more apertures may provide a respective flow path to provide gas to the external environment from the interior of the cavity. The housing may have one or more selectively permeable membranes positioned in respective ones of the flow paths, the selectively permeable membranes selectively blocking moisture from reaching the interior of the cavity from the external environment, and which allow passage of air between the interior and the external environment. The passage of air between the interior and the external environment may allow scent to diffuse from the scent media to the external environment. Air with or without scent may passively diffuse along the respective flow path.

The scent dispensing device of claim 4 may include at least one scent cartridge that carries a first scent media and at least a second scent media, the second scent media different from the first scent media. The first scent media may comprise a fibrous material (e.g., felt or other nonwoven material, clumps, woven or knitted material) saturated with a scent or fragrance (e.g., essential oil). The second scent media may comprise a wax or similar material bearing scent particles. The scent particles may be suspended in the wax material.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 1A is a perspective view of a scent dispensing device having a first size and dimension that is couplable to a first plurality of objects.

FIG. 1B is a perspective view of the scent dispensing device having a second size and dimension that is couplable to a second plurality of objects.

FIG. 2A is a perspective view of the scent dispensing device sized and dimensioned for receiving a first number of scent cartridges.

FIG. 2B is a perspective view of the scent dispensing device sized and dimensioned for receiving the first number of scent cartridges with a housing of the scent dispensing device in a partially open position.

FIG. 2C is an exploded perspective view of the scent dispensing device sized and dimensioned for receiving the first number of scent cartridges.

FIG. 3A is a perspective view of the scent dispensing device sized and dimensioned for receiving a second number of scent cartridges.

FIG. 3B is a perspective view of the scent dispensing device sized and dimensioned for receiving the second number of scent cartridges with the housing of the scent dispensing device in the partially open position.

FIG. 3C is an exploded perspective view of the scent dispensing device sized and dimensioned for receiving the second number of scent cartridges.

FIG. 6A is a perspective view of the scent dispensing device having a safety pin attachment assembly in the open position.

FIG. 6B is a perspective view of the scent dispensing device having the safety pin attachment assembly in the closed position.

FIG. 6C is a perspective view of the scent dispensing device having the safety pin attachment assembly in the open position.

FIG. 6D is a perspective view of the scent dispensing device attached to a textile using the safety pin attachment assembly.

FIG. 11A is a perspective view of a scent dispensing device having a housing sized and dimensioned for receiving a scent cartridge and for releasable attachment to a grommet set in textile in accordance with at least one illustrated embodiment.

FIG. 11B is a perspective view of a scent dispensing device having a housing sized and dimensioned for receiving an unwoven scent cartridge and for releasable attachment to a grommet set in textile in accordance with at least one illustrated embodiment.

FIG. 11C is a perspective view of a scent dispensing device having a housing sized and dimensioned for releasable attachment to a grommet set in textile in accordance with at least one illustrated embodiment.

FIG. 13A is a perspective view of the upper and lower portions of the housing of the scent dispensing device in accordance with one illustrated embodiment.

FIG. 13B is a top view of the lower portion of the housing of the scent dispensing device in accordance with one illustrated embodiment.

FIG. 13C is a side view of the lower portion of the housing of the scent dispensing device in accordance with one illustrated embodiment.

FIG. 13D is a cross-sectional view and a cross-sectional perspective view of the lower portion of the housing of the scent dispensing device taken across line A-A' in FIG. 13B.

FIG. 13E is a bottom view of the lower portion of the housing of the scent dispensing device in accordance with one illustrated embodiment.

DETAILED DESCRIPTION

Figure 4:
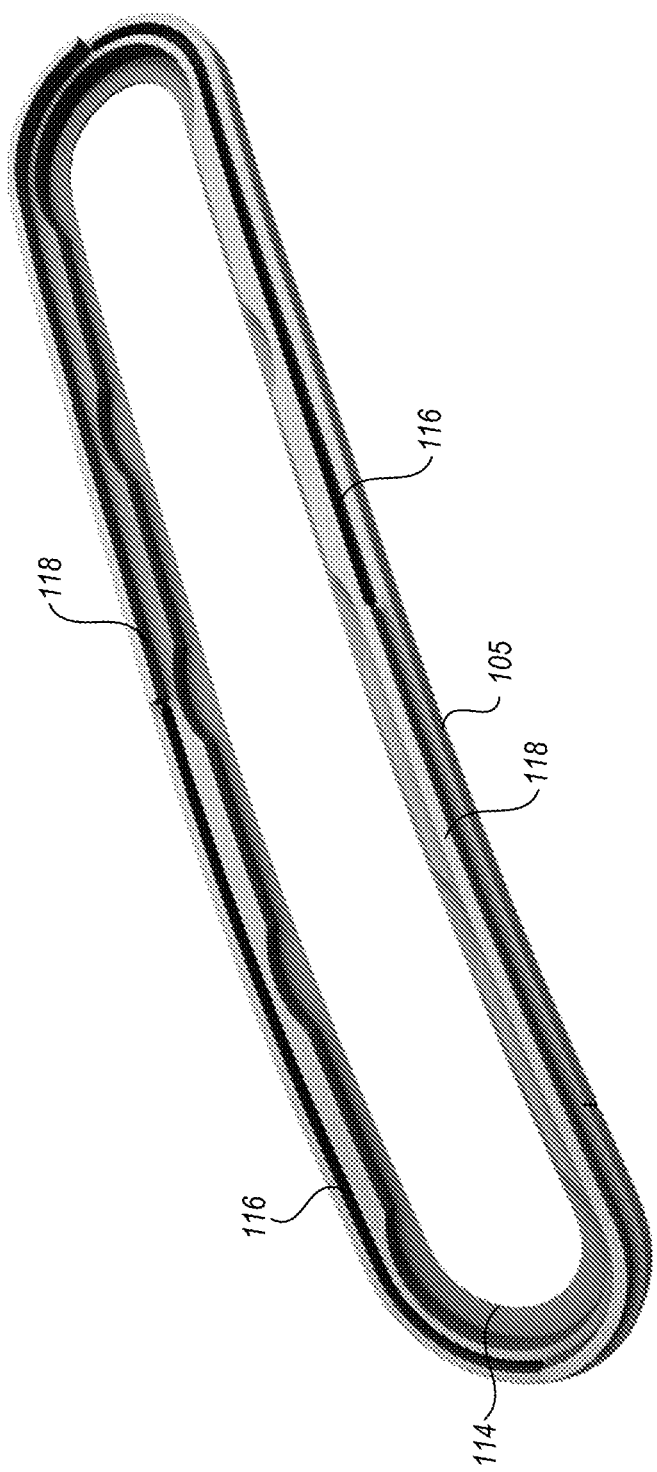
FIG. 4 is a perspective view of a lower portion of the housing of the scent dispensing device sized and dimensioned for receiving the second number of scent cartridges.
Figure 5A:
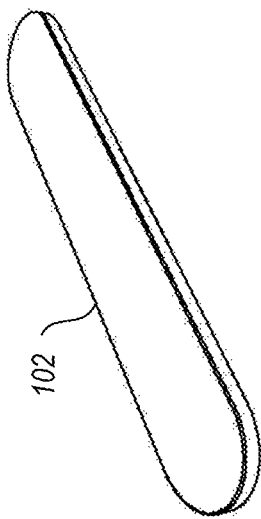
FIG. 5A is a top view of the scent dispensing device in accordance with one illustrated embodiment.
Figure 5B:
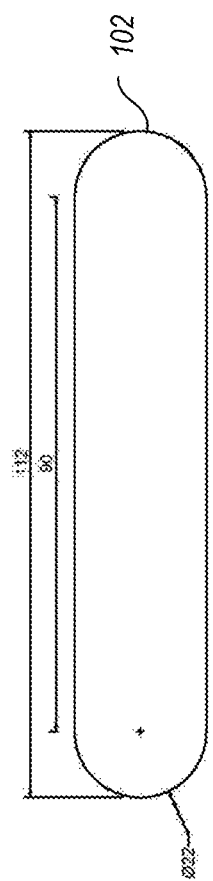
FIG. 5B is a perspective view of the scent dispensing device in accordance with one illustrated embodiment.
Figure 5C:
FIG. 5C is a side view of the scent dispensing device in accordance with one illustrated embodiment.
Figure 5D:
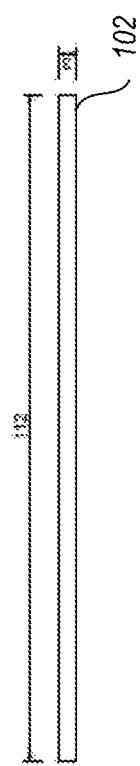
FIG. 5D is a front view of the scent dispensing device in accordance with one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

FIG. 1A shows an example of a scent dispensing device 100a in accordance with at least one embodiment. The scent dispensing device 100a may be used to dispense scent to an environment that is external to the scent dispensing device 100a, to induce a olfactory sensation in a human. The scent dispensing device 100a may be physically coupled to any object, such as a garment or a clothing accessory. If the object is made of textile material, the scent dispensing device 100a may be sewn directly to or into the object. As shown in FIG. 1A, the scent dispensing device 100a may be sewn in as a collar stay for a shirt or in a wristband or cuff of a glove. A person donning the shirt or the glove may smell the scent emanating from the scent dispensing device 100a. Accordingly, the scent dispensing device 100a may be used in lieu of perfume or other body-worn scent.

The scent dispensing device 100a may have various sizes and dimensions. For example, the size or dimensions of the scent dispensing device 100a may be in accordance with that of an article of clothing, accessory or another object to which the scent dispensing device 100a is coupled or physically secured. Furthermore, the scent dispensing device 100a may be deformable and may conform to the article of clothing or accessory to which the scent dispensing device 100a is physically coupled. The scent dispensing device 100a may be elastically deformable to conform to the article of clothing or accessory, so that the scent dispensing device 100a does not interfere with a shape, style or layout of the article or accessory. This allows the article or accessory to retain its aesthetic and functional forms. Accordingly, the scent dispensing device 100a may be used to complement the aesthetic and functional forms of the article or accessory by providing a pleasing scent without conflicting with the shape thereof.

FIG. 1B shows an example of a scent dispensing device 100b in accordance with at least one embodiment. The scent dispensing device 100b shown in FIG. 1B may be of a different size or dimension than the scent dispensing device 100a described with reference to FIG. 1A. The scent dispensing device 100b may be used as a wristband or bracelet or sewn within the wristband so as to be securable to an internal contour of the wristband. Furthermore, the scent dispensing device 100b may be sewn into and secured to a scarf end or a flap of a hand purse. The size and dimension of the scent dispensing device 100a described with reference to FIG. 1A may facilitate coupling the scent dispensing device 100a to different objects than the scent dispensing device 100b described with reference to FIG. 1B. For example, the scent dispensing device 100a may be coupled to a shirt collar as a collar stay, whereas the size or dimension of the scent dispensing device 100b may not permit its use as a collar stay. It is noted that scent dispensing devices 100 are collectively referred to herein by the numeral alone.

FIGS. 2A-2C show a scent dispensing device 100a, according to the embodiment of FIG. 1A. The scent dispensing device 100a has a housing 102, which is illustrated in a closed position in FIG. 2A and a partially open position in FIG. 2B. The housing 102 of the scent dispensing device 100a has an upper portion 103 and a lower portion 105 that are removably coupled to one another. Further, the upper portion 103 and the lower portion 105 of the housing 102 may be resiliently deformable so as to enable their physical decoupling to gain access to one or more scent cartridges received therein as described herein. For example, the upper portion 103 and the lower portion 105 may be made from a supple and/or resilient material, such as supple silicon, and may accordingly be elastically bendable and conformable.

As may be best viewed in FIG. 2C, the housing 102 of the scent dispensing device 100a has a cavity 104 that forms the interior 107 of the housing 102 and the housing 102 separates the interior 107 from an external environment 109. The cavity 104 is sized and dimensioned to removably receive one or more scent cartridges 106. The housing 102 may be configured with a receiver (such as a tab) that releasably secures the one or more scent cartridges 106 in the cavity 104 of the housing 102. The housing 102 or the upper portion 103 or lower portion 105 thereof may each also include a respective aperture 108a, 108b. The apertures 108a, 108b provide a flow path between the interior of the housing and the external environment so as to provide gas communication between the interior and the external environment. Fresh air may enter the housing 102 along a flow path provided by a first aperture 108a and scented air may exit the housing 102 along a flow path provided by a second aperture 108a of the housing 102.

The scent dispensing device 100a also has a one or more selectively permeable membranes 110a, 110b (two illustrated). The selectively permeable membranes 110a, 110b may each be associated with a respective aperture 108a, 108b of the housing 102. The selectively permeable membranes 110a, 110b may be positioned in the flow path provided by the apertures 108a, 108b between the interior of the housing 102 and the external environment. The selectively permeable membranes 110a, 110b may selectively block moisture from the external environment from reaching the interior of the housing 102. The selectively permeable membranes 110a, 110b may, conversely, permit passage of gas between the interior of the housing 102 and the external environment including passage of at least one scent from the interior of the housing 102 to the external environment. Similar to the housing 102, the selectively permeable membranes 110a, 110b may also be elastically and/or resiliently bendable and resiliently conformable.

Air with or without scent may passively diffuse along a flow path and through a permeable membrane 100 (collectively referred to herein by the numeral alone). The air may be passively convectively conveyed or transferred within the interior 107 or from the interior 107 to the external environment 109 without being actively driven (for example, with the aid of a fan or an air jet).

As described herein, a scent cartridge of the one or more scent cartridges 106 may hold one or more scent media. The scent media may be in any form, such as liquid, solid or gas. In various embodiments, a scent cartridge 106 may be a wick that is twisted, braided or woven and made to absorb a liquid scent that is the scent media. The scent media may also be scented wax or powder.

A scent cartridge 106 may have any shape. For example, the scent cartridge 106 may be a disk having a radius that is greater than 5 or 10 millimeters (mm) and a height that is greater than 1 mm. Accordingly, an operator of the scent dispensing device 100 (for example, a human) may conveniently handle and manually manipulate the scent cartridge 106 when replacing a depleted scent cartridge 106 or swapping a scent cartridge 106 emanating one type of scent with another emanating a different type of scent. A person may carry multiple scent cartridges 106 (for example, in a scent cartridge holder) and may swap out the scent cartridge 106 of the scent dispensing device 100 with another scent cartridge 106 emanating a different scent depending on the scent the person wishes to wear.

The scent cartridge 106 may have a plurality of chambers 112, whereby a chamber of the plurality of chambers 112 is configured to hold a scent medium. A scent medium associated with one chamber may be different from a scent medium of another chamber. Scent provided by a scent medium, which may be any type of aroma compound, such as an essential oil, may combine with that emanating from another to compose aroma. A scent cartridge 106 holding a plurality of scent media may be used to produce various aromas. For example, aroma emanating from the scent dispensing device 100 may be chosen by selectively blocking passage from certain scent media and permitting passage from other scent media. The combination of scent emanating from the scent media may form a desired scent. For example, a scent cartridge 106 having five scent media may be used to produce $$\binom{5}{1}+\binom{5}{2}+\binom{5}{3}+\binom{5}{4}+\binom{5}{5}=5+10+10+5+1=31$$

different aromas. If a scent cartridge has n scent cartridge chambers, the maximum number of potential scent combinations obtained from the scent cartridge (denoted as m) may be obtained as:

$$m=\sum_{r=1}^{n}\frac{n!}{r!(n-r)!},$$

where the symbol '!' denotes the factorial operator.

To increase the longevity of the scent media held by the one or more scent cartridges 106, it may be advantageous for the air circulating through the scent dispensing device 100a to be moisture-free. The selectively permeable membranes 110a, 110b may permit the passage of dry air therethrough but may be constructed to block the passage of moisture. For example, the selectively permeable membranes 110a, 110b may be made from hydrophobic or lipolithic woven or nonwoven material that inhibits the passage of moisture from the exterior environment to the interior and instead causes droplets of moisture to collect on an exterior surface of the selectively permeable membranes 110a, 110b. Due to the fact that materials having an affinity to fat (i.e., lipophilic materials) are typically water repellant, the selectively permeable membranes 110a, 110b may in many circumstances be composed of a material having lipophilic properties.

To increase the longevity or the "useful life" of the scent cartridges 106, it may be advantageous to employ multiple (e.g., two or more) layers of scent media in the scent cartridges 106. For example, the scent cartridges 106 may each include a first layer of scent media and a second layer of scent media, the second layer distinct and separate from the first layer of scent media. For instance, the first layer of scent media may take the form of a scent saturated fibrous material or fabric (e.g., felt or other nonwoven material, clumps, woven or knitted material). The fibrous material is saturated with fragrance (e.g., essential oil(s)), and optionally dried before being placed in a housing or retaining structure of the scent cartridge. For instance, the second layer may take the form of a scent impregnated or containing wax or similar material, for instance with a suspension of fragrance particles suspended therein. It may be advantageous to located the scent saturated fibrous material or fabric relatively closer to a portion of the scent cartridge that will be proximate an end users nose in use, relative to the scent impregnated or containing wax or similar material. The scent saturated fibrous material or fabric will tend to allow passage therethrough of scent originating from the from the scent impregnated or containing wax or similar material.

Using two or more layers with different scent dispersion characteristics or different scent dispersion profiles in a scent cartridge 106 may advantageously prolong the useful life of the scent cartridge. Where the respective scent dispersion profiles are inverse or at least somewhat complementary, such may advantageously result in a more uniform performance over the useful life of the scent cartridge 106. Further, using two or more layers with different scent dispersion characteristics in a scent cartridge 106 may advantageously reduce the amount of liquid scent or fragrance required to achieve a desired level of scent dispersion, thereby reducing or eliminating the possibility of leakage from the scent cartridge.

The first, the second, and any additional layers of scent media may be retained in a housing or retaining structure, for instance an annulus or ring structure having a perimeter or periphery. The housing or retaining structure may, for example, comprise a plastic or similar material. In particular, housing or retaining structure may comprise a material that is non-reactive to the scent media or fragrance (e.g., essential oils), and which forms a seal to prevent leakage from the scent cartridge 106. The first, the second, and any additional layers of scent media may be sandwiched or spaced between the selectively permeable membranes 110a, 110b, which may permit the passage of dry air therethrough but may be constructed to block the passage of moisture. For example, the selectively permeable membranes 110a, 110b may be made from hydrophobic or lipophilic woven or nonwoven material that inhibits the passage of moisture from the exterior environment to the interior and instead causes droplets of moisture to collect on an exterior surface of the selectively permeable membranes 110a, 110b. Due to the fact that materials having an affinity to fat (i.e., lipophilic materials) are typically water repellant, the selectively permeable membranes 110a, 110b may in many circumstances be composed of a material having lipophilic properties.

While generally described above as having two layers of two different types of scent media, a scent cartridge 106 may employ more than two layers of the two different types of scent media. Additionally, or alternatively, a scent cartridge 106 may employ more than two layers of more than two different types of scent media (e.g., three layers, one each of three different types of scent media). Some of the scent media may be passive, emitting scent without any particular stimulus, while some of the scent media may require activation via a particular stimulus (e.g., application of water, heat, vibratory motion) to emit scent.

FIGS. 3A-3C and 4 show a scent dispensing device 100b according to the embodiment of FIG. 1B. The scent dispensing device 100b has a housing 102 which is illustrated in a closed position in FIG. 3A and in a partially open position in FIG. 3B. The scent dispensing device of FIG. 3A is similar to those described with reference to FIGS. 2A-C. However, the scent dispensing device 100b of FIG. 3A is sized and dimensioned to receive and retain five scent cartridges 106, whereas the scent dispensing device 100a described with reference to FIGS. 2A-C is sized and dimensioned to only retain two scent cartridges 106.

As best illustrated in FIG. 4 shows a perspective view of a lower portion 105 of the housing 102 of the scent dispensing device 100b described with reference to FIGS. 3A-C. As described herein, the lower portion 105 of the housing 102 is removably couplable to the upper portion of the housing (not shown). A first surface 114 of the lower portion 105 has one or more grooves 116 and one or more tongues 118. The one or more grooves 116 of the lower portion 105 are sized and dimensioned to engagingly receive one or more tongues disposed on a second surface of the upper portion. Furthermore, the one or more tongues 118 are sized and dimensioned to be engagingly received by one or more grooves (not shown) also disposed on the second surface of the upper portion. Accordingly, the upper and lower portions may be detachably secured together to form the housing 102.

As described herein, the scent dispensing device 100 may be worn on a biological body or attached to, mounted on or otherwise associated with an article of clothing or another object. The scent dispensing device 100 may, for example, be worn as a bracelet as shown in FIG. 1A or may be sewn around secured to an internal contour of the bracelet. Furthermore, the scent dispensing device 100 may be coupled to an article of clothing or dress accessory by sewing fabric around the scent dispensing device 100. Non-limiting examples of garments to which the scent dispensing device 100 may be attached include a scarf, glove or shirt or collar thereof. Non-limiting examples of dress accessories to which the scent dispensing device 100 may be attached include a purse, wallet, handbag or backpack. In addition, the scent dispensing device 100 may be associated with various articles of manufacture. For example, the scent dispensing device 100 may be incorporated into drywall and may thus be used to provide an aroma to the interior of structures, such as homes, offices or public areas. In addition, the scent dispensing device 100 may be incorporated into motor vehicles for dispensing scent to drivers and passengers. For example, the scent dispensing device 100 may be part of a car seat, dashboard, liner, or a sun visor and may, thus, emanate scent through an interior of a car.

Figure 7:
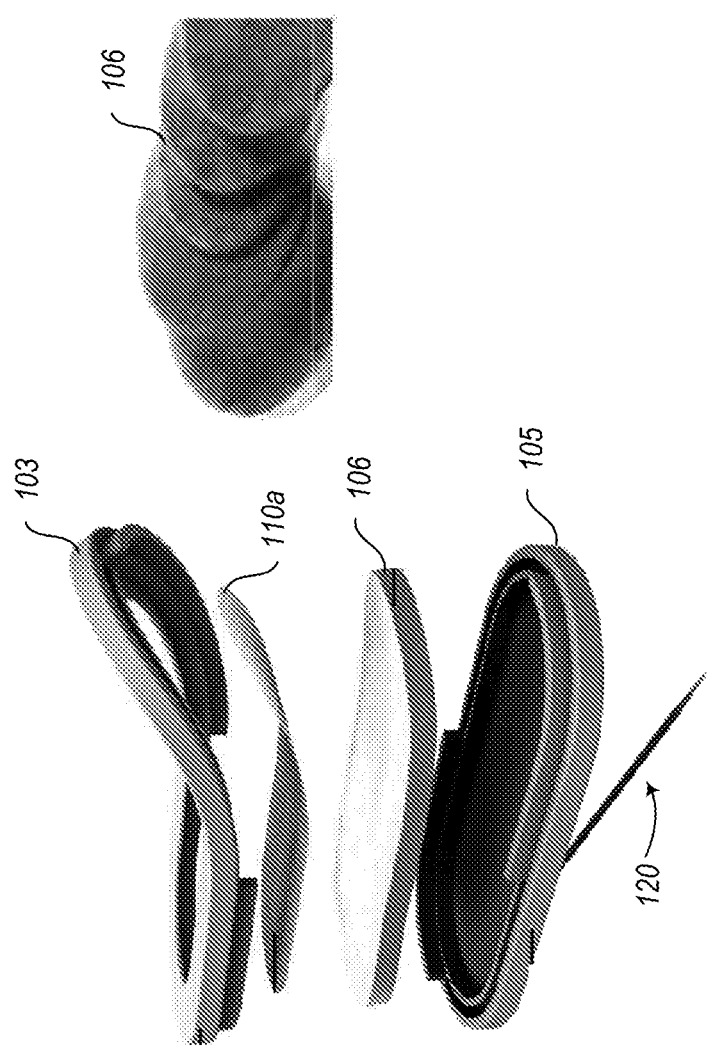
FIG. 7 is an exploded perspective view of the scent dispensing device sized and dimensioned for receiving an unwoven scent cartridge and having the safety pin attachment assembly.
Figure 8A:
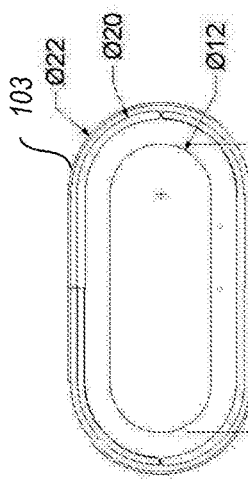
FIG. 8A is a perspective view of an upper portion of the housing of the scent dispensing device in accordance with one illustrated embodiment.
Figure 8B:
FIG. 8B is a top view of the upper portion of the housing of the scent dispensing device in accordance with one illustrated embodiment.
Figure 8C:
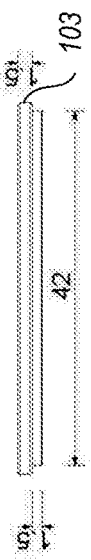
FIG. 8C is a front view of the upper portion of the housing of the scent dispensing device in accordance with one illustrated embodiment.
Figure 8D:
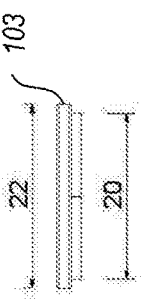
FIG. 8D is a side view of the upper portion of the housing of the scent dispensing device in accordance with one illustrated embodiment.
Figure 9A:
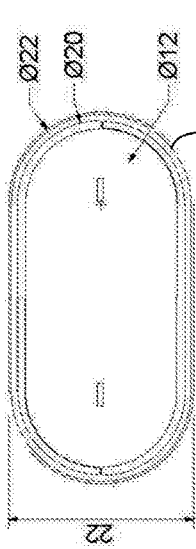
FIG. 9A is a perspective view of a lower portion of the housing of the scent dispensing device having the safety pin attachment assembly.
Figure 9B:
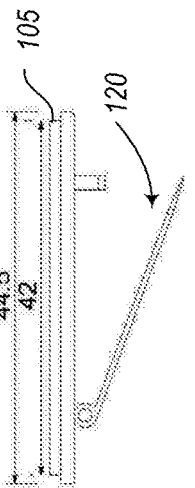
FIG. 9B is a top view of the lower portion of the housing of the scent dispensing device having the safety pin attachment assembly.
Figure 9C:
FIG. 9C is a front view of the lower portion of the housing of the scent dispensing device having the safety pin attachment assembly in the open position.
Figure 9D:
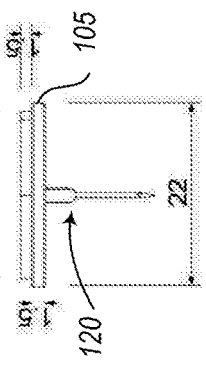
FIG. 9D is a side view of the lower portion of the housing of the scent dispensing device having the safety pin attachment assembly in the open position.

The scent dispensing device 100 may be removably attached to an object in a variety of ways including use of a safety pin assembly. The safety pin assembly may be used to pin the device to the object. Furthermore, the scent dispensing device 100 may be removably attached by attachment to a grommet that is set in the object. A scent dispensing device 100c equipped with a safety pin assembly 120 is shown in FIGS. 6A, 6B and 7. The safety pin assembly 120 may be disposed on an exterior surface 124 of the lower portion 105 of the housing 102. The safety pin assembly may be used for attachment of the scent dispensing device 100c to a textile 122 as shown in FIG. 6D.

Figure 10B:
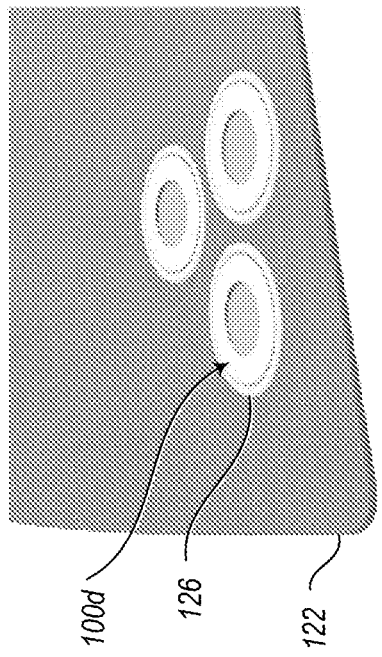
FIG. 10B is a perspective view of an example of attachment of a plurality of scent dispensing devices to a plurality of grommets set in textile.
Figure 10A:
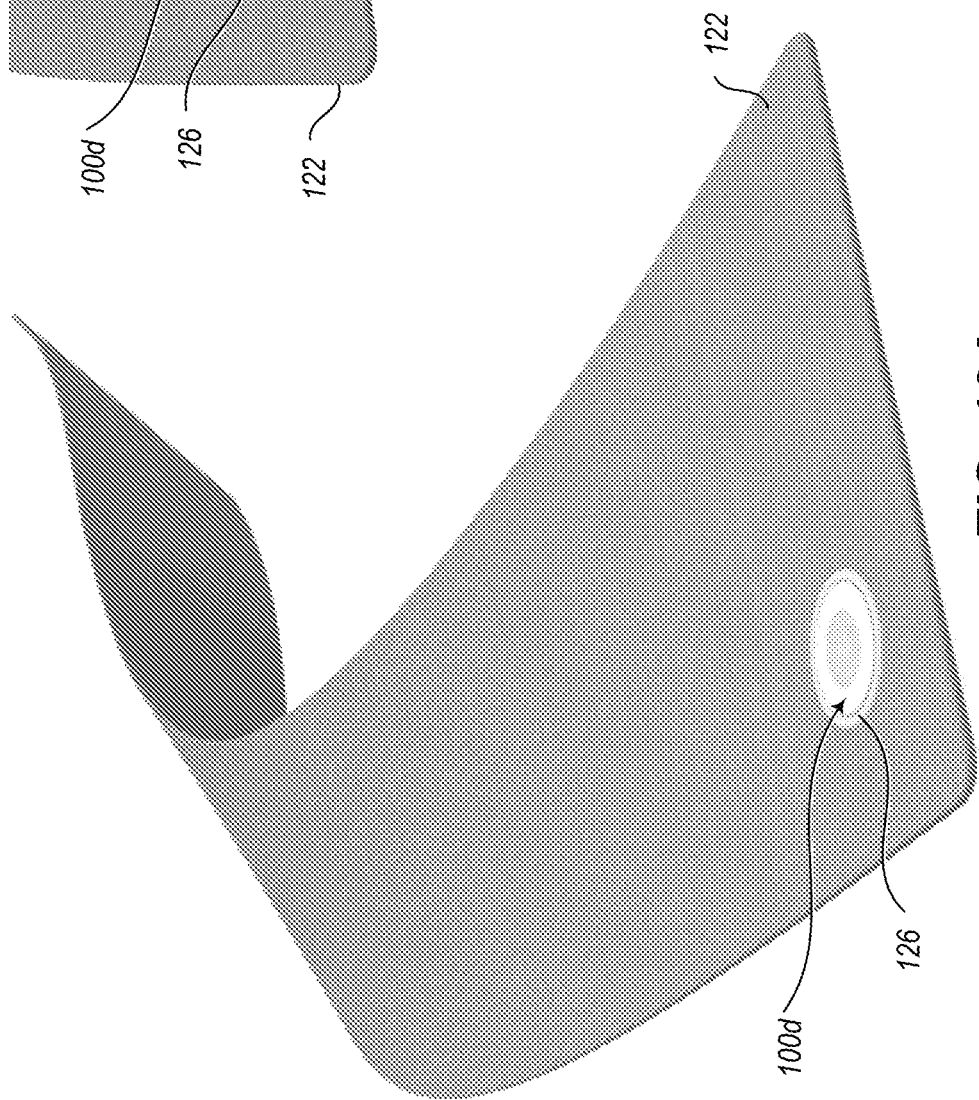
FIG. 10A is an example of attachment of the scent dispensing device to a grommet set in textile.
Figure 12:
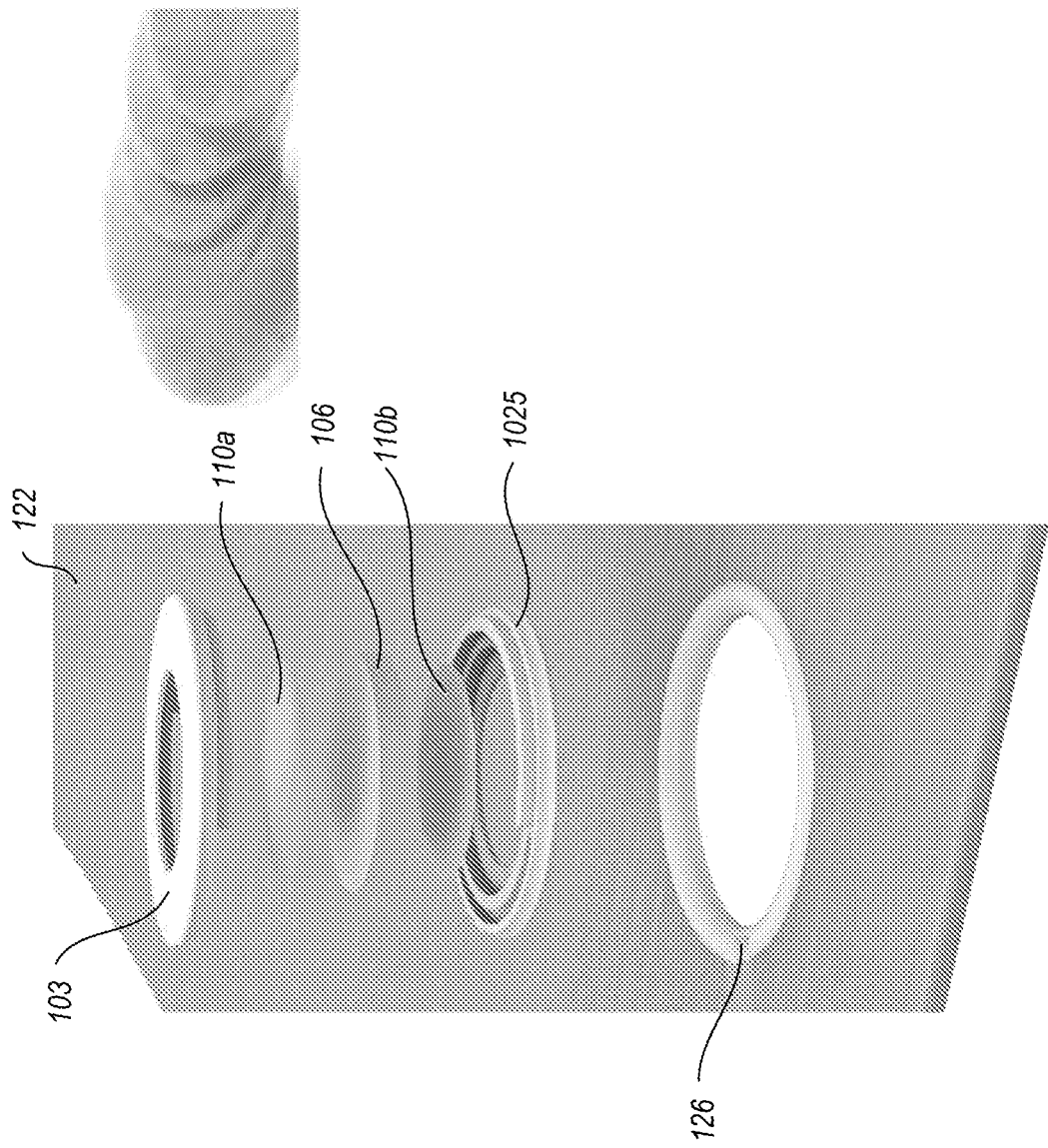
FIG. 12 is an exploded perspective view of the scent dispensing device having a housing sized and dimensioned for releasable attachment to a grommet set in textile in accordance with at least one illustrated embodiment.

FIGS. 10A, 10B and 11C show an example of releasable attachment of a scent dispensing device 100d to an object using a grommet 126 set in the object. The grommet 126 may be set in textile 122 or another material and may define a passage used to at least partially secure the scent dispensing device 100. In various embodiments, the housing 102 of the scent dispensing device 100d may be elastically and/or resiliently deformable to be removably received and secured in the passage of the grommet 126. The grommet 126 may be made of metal, plastic or other material and may or may not be deformable. Further, the grommet 126 may be non-deformable and an elastically and/or resiliently deformable ring, such as an O-ring, may be carried on or by an inner periphery of the grommet 16. The deformable ring may be used to removably engage the scent dispensing device 100d or the housing 102 thereof, which, as described herein, may itself be deformable or non-deformable. Alternatively, the grommet 126 may be elastically and/or resiliently deformable and may removably engage the scent dispensing device 100d or the housing 102 thereof, which may itself be deformable or non-deformable.

The deformablility of the scent dispensing device 100d, housing 102 thereof, ring or the grommet 126 enables releasable coupling of the scent dispensing device 100d to the textile 126 or other material in which the grommet 126 is set. For example, when the scent dispensing device 100d is engaged with the grommet 126, the application of force to the scent dispensing device 100d results in the release of the scent dispensing device 100d.

As shown in FIG. 10B, multiple scent dispensing devices 100 may be attached to an object, such as the textile 122. One or more scent dispensing devices 100 each emanating the same or different aromas may be releasably secured to one or more grommets 126. A scent dispensing devices 100 be swapped with another scent dispensing device 100 by a person wearing the textile to change their aroma or obtain a desired aroma. Alternatively, the same scent dispensing device 100 may be used but the scent cartridge 106 received by the scent dispensing device 100 may be swapped with another scent cartridge 106 emanating a different aroma. As described herein, if a combination of aromas is desired, two or more scent dispensing devices 100 may be releasably secured to two or more grommets 126. Further, if a scent cartridge 106 of a scent dispensing device 100 is depleted, the scent dispensing device 100 or the cartridge 106 thereof may be substituted.

As may be best viewed in FIGS. 13A and 13B, the upper portion 103 and the lower portion 105 of the housing 102 of the scent dispensing device 100d may each be annular-shaped. Disposed on an outer periphery of an interior surface of the lower portion 105 is a groove 130 and a tongue 132. The groove 130 may span a first arc on the outer periphery and the tongue 132 may span a second arc on the outer periphery, whereby the first and second arcs may be non-overlapping and may combine to substantially form a circle. Similar to the lower portion 105, the upper portion 103 also has an interior surface, and the interior surface has disposed thereon a groove sized and dimensioned to securingly receive the tongue 132 of the lower portion 105 when the housing is in a closed or partially closed position. In addition, the interior surface of the upper portion 103 also has disposed thereon a tongue sized and dimensioned to be securingly received by the groove 130 of the lower portion 105 when the housing is in a closed or partially closed position.

Figure 14:
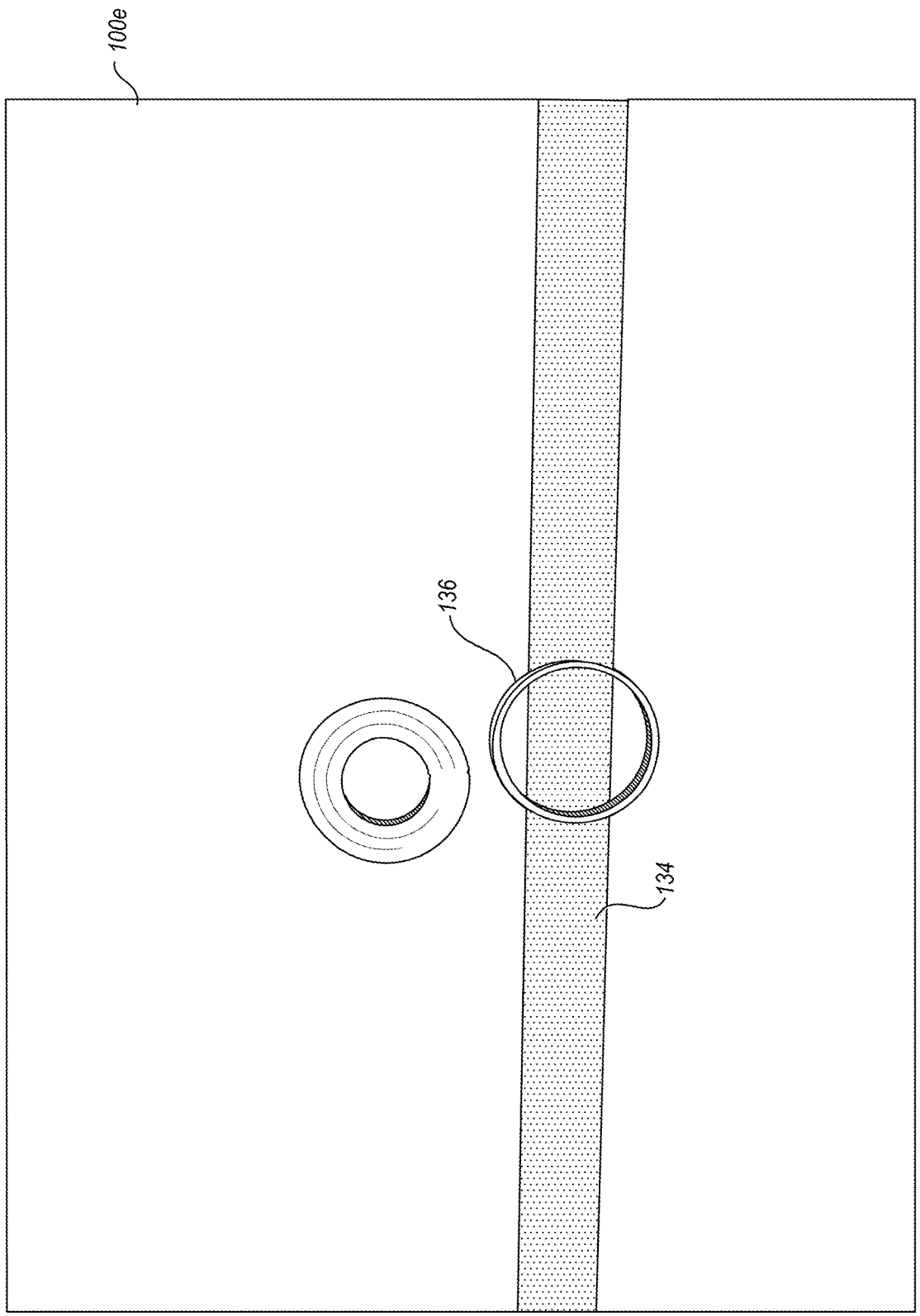
FIG. 14 is a top view of an example of a scent dispensing device coupled to wrist strap in accordance with one illustrated embodiment.

FIG. 14 shows an example of a scent dispensing device 100e sized and dimensioned for coupling to a wrist band 134 that may be worn on a human wrist. The wrist band 134 has a compartment 136 sized and dimensioned for receiving the scent dispensing device 100e and releasably securely holding the scent dispensing device 100e in the compartment 136.

In various embodiments, the scent dispensing device 100 may also include an interface for facilitating communication with the scent dispensing device 100. For example, the interface may be electrical, optical or inductive, among others contemplated by those skilled in the art (e.g., electrical contacts or terminals). The interface, which may be wired or wireless, may be used for configuring the operation of the scent dispensing device 100. For example, the interface may be used to connect the scent dispensing device 100 to a computing device and carry data therebetween. The computing device may be used by a user to configure the operation of the scent dispensing device 100. Configuring the operation of the scent dispensing device 100 may include selecting the scent to be dispensed by the device or configuring an air flow through the scent dispensing device 100. The air flow may be adjusted such that to regulate the intensity of the scent emanating from scent dispensing device 100.

For example, the scent dispensing device 100 may be configured with a fan or an air jet, such as a synthetic air jet, among others. The fan or air jet may be positioned and selectively operable to cause a flow of air between the interior of the housing of the scent dispensing device 100 and the external environment so as to actively diffuse scent into the external environment.

In various embodiments, a selectively permeable membrane 110 of the scent dispensing device 100 may be constructed of fabric of another material. The fabric or material may be porous, whereby pores may have certain cross-sectional areas. The sizes of the cross-sectional areas may dictate the volume or rate of the scent emanating from the scent dispensing device 100, whereby as the size of a cross-sectional area decreases so does the volume or rate of the emanating scent. The sizes cross-sectional areas of the pores may be dynamically changeable based at least in part on electrical current supplied to the fabric of another material thus permitting changing a mode of operation of the scent dispensing device 100. For example, the scent dispensing device 100 may in an 'off' mode if the pore cross-sectional areas are reduced to a minuscule amount.

The various embodiments described above can be combined to provide further embodiments. To the extent that they are not inconsistent with the specific teachings and definitions herein, U.S. patent application Ser. Nos. 62/116,258, filed Feb. 13, 2015; 62/153,936, filed Apr. 28, 2015; all of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ systems, circuits and concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A scent dispensing device comprising:
   a housing that has a cavity that forms an interior of the housing, the housing which separates the interior from an external environment which is external to the housing, the interior sized and dimensioned to receive one or more scent cartridges, the housing having a number of apertures which provide respective ones of a number of flow paths between the interior of the housing and the external environment, the housing having at least one portion that is resiliently deformedly physically securable in an internal contour of at least a portion of an object to which the scent dispensing device is physically securable; and
   a number of selectively permeable membranes positioned in the flow paths, the selectively permeable membranes which selectively block moisture from reaching the interior of the housing from the external environment, and which permit passage of gas between the interior of the housing and the external environment including passage of at least one scent from the interior of the housing to the external environment.

2. The scent dispensing device of claim 1 wherein the housing includes at least one scent cartridge receiver, the at least one scent cartridge receiver sized and dimensioned to secure the at least one scent cartridge in the cavity of the housing.

3. The scent dispensing device of claim 2, further comprising:
   at least one scent cartridge which carries at least one scent media, the at least one scent cartridge securely received by the at least one scent cartridge receiver.

4. The scent dispensing device of claim 2, further comprising:
   at least one scent cartridge which carries at least one scent media, the at least one scent cartridge securely removably received by the at least one scent cartridge receiver.

5. The scent dispensing device of claim 4 wherein the at least one scent cartridge which carries a first scent media and at least a second scent media, the second scent media different from the first scent media.

6. The scent dispensing device of claim 5 wherein the first scent media comprises a saturated fibrous material.

7. The scent dispensing device of claim 6 wherein the second scent media comprises a wax material bearing scent particles.

8. The scent dispensing device of claim 7 wherein the scent particles are suspended in the wax material.

9. The scent dispensing device of claim 7 wherein the saturated fibrous material is positioned in the at least one scent cartridge toward an output face of the scent cartridge relative to the wax material, the output face placed relatively closer to a nose in use than an opposed face of the output cartridge.

10. The scent dispensing device of claim 1 wherein at least one selectively permeable membrane is a hydrophobic membrane.

11. The scent dispensing device of claim 1, further comprising:
    at least one of a fan or a synthetic jet positioned and selectively operable to cause a flow of air between the interior of the housing and the external environment to diffuse scent into the external environment.

12. The scent dispensing device of claim 1, further comprising:
    an interface that transfers data to the scent dispensing device.

13. The scent dispensing device of claim 12 wherein the data specifies at least one of a selection of the scent provided by the scent dispensing device or a setting of at least one of a fan or a synthetic jet of the scent dispensing device, the setting indicating an operational mode of the at least one of a fan or a synthetic jet.

14. The scent dispensing device of claim 1 wherein at least one portion of at least an exterior of the housing is resiliently deformedly physically securable in an internal contour of at least a portion of an object to which the scent dispensing device is physically securable.

15. The scent dispensing device of claim 1 wherein the at least one scent passively diffuses along the flow path and through the selectively permeable membranes positioned in the flow path.

16. The scent dispensing device of claim 1 wherein the at least one scent is passively convectively conveyed along the flow path and through the selectively permeable membranes positioned in the flow path.

17. A scent dispensing device, comprising:
    an object having an internal contour; and
    a housing that has a cavity that forms an interior of the housing, the housing which separates the interior from an external environment which is external to the housing, the interior sized and dimensioned to receive one or more scent cartridges, the housing having at least one aperture which provides at least one flow path between the interior of the housing and the external environment, and the housing having an exterior periphery that is resiliently deformable and sized to be resiliently deformedly physically securable in the internal contour of at least a portion of the object with the resiliently deformable exterior peripheral portion in contact with the internal contour of the object over an entirety of a closed path about the exterior periphery of the housing when secured in the internal contour of the object.

18. The scent dispensing device of claim 17 wherein the housing is removably physically secured to the object via at least a friction or an interference fit therewith.

19. The scent dispensing device of claim 17, further comprising:
    one or more scent cartridges disposed in the interior of the scent dispensing device, at least one of the one or more scent cartridges carries one or more scent media.

20. The scent dispensing device of claim 19 wherein the housing further includes at least one scent cartridge receiver, the at least one scent cartridge receiver sized and dimensioned to removably secure the at least one scent cartridge in the cavity of the housing.

21. The scent dispensing device of claim 17 wherein the object comprises:
    a grommet having a passage that extends through the grommet and that delineates the internal contour; and
    the housing removably resiliently securable at least partially in the passage of the grommet.

22. The scent dispensing device of claim 17 wherein the object comprises a textile with a grommet that is attached to the textile, the grommet having a passage that extends therethrough, and at least a portion of the housing is resiliently deformable to removably physically secure the housing at least partially in the passage of the grommet.

23. The scent dispensing device of claim 21 wherein the housing comprises an upper portion and a lower portion, the upper portion and the lower portion are removably coupled to one another to enable removable replacement of at least one scent cartridge which carries the scent media.

24. The scent dispensing device of claim 23 wherein at least one of the upper portion or the lower portion has a first surface with groove disposed thereon, the groove is sized and dimensioned to receive a tongue disposed on a second surface of at least another one of the upper portion or the lower portion and removably hold the at least another one of the upper portion or the lower portion.

25. The scent dispensing device of claim 17 wherein the interior of the housing encloses the one or more scent cartridges received therein even when the housing is not secured to the object.

26. A scent dispensing device, comprising:
a housing that has a cavity that forms an interior of the housing, the housing which separates the interior from an external environment which is external to the housing, the interior sized and dimensioned to receive one or more scent cartridges, the housing having at least one aperture which provides at least one flow path between the interior of the housing and the external environment, and the housing having at least one portion that is resiliently deformedly physically securable in an internal contour of at least a portion of an object, wherein the at least one scent cartridge carries a first scent media and at least a second scent media, the second scent media different from the first scent media, the first scent media comprises a saturated fibrous material or a wax material bearing scent particles.

\* \* \* \* \*